US00PP16903P3

(12) United States Plant Patent
Lintott

(10) Patent No.: US PP16,903 P3
(45) Date of Patent: Aug. 1, 2006

(54) *CHRYSANTHEMUM* PLANT NAMED 'CALABRIA MAJOR'

(50) Latin Name: *Chrysanthemum morifolium*
Varietal Denomination: Calabria Major

(75) Inventor: Keith G. Lintott, Bognor Regis (GB)

(73) Assignee: Cleangro, Ltd, Chichester (GB)

( * ) Notice: Subject to any disclaimer, the term of this patent is extended or adjusted under 35 U.S.C. 154(b) by 101 days.

(21) Appl. No.: 11/055,199

(22) Filed: Feb. 9, 2005

(65) Prior Publication Data

US 2005/0177911 P1 Aug. 11, 2005

Related U.S. Application Data

(60) Provisional application No. 60/544,060, filed on Feb. 11, 2004.

(51) Int. Cl.
*A01H 5/00* (2006.01)

(52) U.S. Cl. ..... Plt./288; Plt./288

(58) Field of Classification Search ..... Plt./288
See application file for complete search history.

(56) References Cited

U.S. PATENT DOCUMENTS

PP10,066 P 10/1997 Wain ..... Plt./77

OTHER PUBLICATIONS

1998 Ficor catalog, listing the variety 'Calabria'. See, e.g., pp. 2 (photograph) and 4–5.
1999 Ficor catalog, listing the variety 'Calabria'. See, e.g., pp. 1 (photograph) and 4–5.
2000 Ficor catalog, listing the variety 'Calabria'. See, e.g., pp. 4–5.
2001 Ficor catalog, listing the variety 'Calabria'. See, e.g., pp. 4 and 10.
2002 Ficor catalog, listing the variety 'Calabria'. See, e.g., pp. 4 and 10.
2003 Ficor catalog, listing the variety 'Calabria'. See, e.g., pp. 2 and 8.
2004 Ficor catalog, listing the variety 'Calabria'. See, e.g., pp. 2 and 8.

*Primary Examiner*—Anne Marie Grunberg
*Assistant Examiner*—Annette H Para
(74) *Attorney, Agent, or Firm*—Winston & Strawn LLP

(57) ABSTRACT

A new variety of *Chrysanthemum* named 'Calabria Major,' having a slightly domed capitulum of large white decorative type flowers.

1 Drawing Sheet

Latin name of the genus and species: Botanical classification: *Chrysanthemum morifolium.*

Variety denomination: The new *Chrysanthemum* variety denomination is 'Calabria Major.'

BACKGROUND OF THE INVENTION

The present invention comprises a new and distinct cultivar of *Chrysanthemum* botanically known as *Chrysanthemum morifolium,* and referred to by the variety name 'Calabria Major.'

'Calabria Major,' identified as 10172-22 originated from a naturally occurring whole plant mutation grown in a controlled planting of the variety 'Calabria' in Chichester, West Sussex, United Kingdom.

The new variety 'Calabria Major' has been asexually reproduced by vegetative cuttings in Chichester, West Sussex, United Kingdom and the distinguishing characteristics are retained through successive generations of asexual reproduction.

BRIEF SUMMARY OF THE INVENTION

'Calabria Major' is a spray cut flower type of *Chrysanthemum* plant variety having flat capitulum of white decorative flowers.

Comparison with Parent

Plants of the new *Chrysanthemum* variety 'Calabria Major' are similar to the parent variety 'Calabria' in plant habit and growth rate. However, in side-by-side comparisons in Chichester, West Sussex, United Kingdom, under commercial practice, plants of the new *Chrysanthemum* variety 'Calabria Major' differed from plants of the parent variety 'Calabria' in the following characteristics.

1. The new *Chrysanthemum* variety 'Calabria Major' produces larger white decorative flowers than the parent variety 'Calabria.'
2. Plants of the new *Chrysanthemum* variety 'Calabria Major' have larger flowers and bigger inflorescence than plants of the parent variety 'Calabria.'
3. Plants of the new *Chrysanthemum* variety 'Calabria Major' are more vigorous than plants of the parent variety 'Calabria.'
4. Plants of the new *Chrysanthemum* variety, 'Calabria Major' flowers 2 to 3 days earlier than plants of the parent variety 'Calabria.'

Comparison with Variety 'White Fiji'

Plants of the new *Chrysanthemum* variety 'Calabria Major' are dissimilar to the variety 'White Fiji' (U.S. Plant Pat. No. 10,066) in plant habit and growth rate. In side-by-side comparisons in Chichester, West Sussex, United Kingdom, under commercial practice, plants of the new *Chrysanthemum* variety 'Calabria Major' differed from plants of the variety 'White Fiji' in the following characteristics.

1. The new *Chrysanthemum* variety 'Calabria Major' produces flat decorative white flowers whereas 'White Fiji' produces incurving white decorative flowers.
2. Plants of the new *Chrysanthemum* variety 'Calabria Major' have a more upright inflorescence than plants of the variety 'White Fiji.'
3. Plants of the new *Chrysanthemum* variety 'Calabria Major,' are more vigorous than plants of the variety 'White Fiji.'
4. Plants of the new *Chrysanthemum* variety 'Calabria Major' require less short days to flower than 'White Fiji.'

BRIEF DESCRIPTION OF ILLUSTRATION

Typical specimens of the plant and flowers for the new *Chrysanthemum* variety 'Calabria Major' are shown in the accompanying digital photograph. The colors shown are as true as possible within the usual limits of this kind of illustration.

FIG. 1 is a whole plant view of the new variety 'Calabria Major' grown as a cut flower.

The plant shown in the illustration is 50 days from the commencement of Short Days.

DETAILED BOTANICAL DESCRIPTION

The following description of the new *Chrysanthemum* variety 'Calabria Major' is of plants grown in a greenhouse, in Chichester, West Sussex, United Kingdom in the month of July. The variety has not been observed under all possible environmental conditions. The phenotype may vary significantly with variations in the environment such as temperature, length of day and light intensity, without any variance in genotype. The commercial classification of the new variety is a cut flower *Chrysanthemum.*

Plants of the new *Chrysanthemum* variety have been grown successfully under temperature conditions averaging about 18° C. at night and about 18° C. to 24° C. during the day under light conditions of about 5000 to 6000 foot candles. The plants respond well to the use of growth retardant, such as one B9 treatment at about 1 gram/liter 7 days after the commencement of Short Days. To produce a commercial product the plants should have 14 Long Days before commencement of Short Days and the center bud has to be removed about 4 weeks before flowering. It has been observed that the shelf life of the new variety is about 18 days with a response time of about 7½ weeks. The new variety is suitable for growth in a temperature range of 18° C. to 24° C.

The new variety may be produced as a spray *Chrysanthemum.* The following description is with respect to a plant produced as cut flower *Chrysanthemum.* In the description of this new *Chrysanthemum* variety, color values have been taken from The Royal Horticultural Society Colour (R.H.S.C.C.).

Plant

Plant type: Decorative type cut *Chrysanthemum.*
Habit: Upright, flat capitulum.
Height: 75 cm–90 cm.
Width: 14 cm–19 cm.
Stem:
- *Length.*—80 cm–90 cm.
- *Diameter.*—0.7 cm–0.9 cm.
- *Texture.*—Slightly pubescent.
- *Color.*—Near 146B.

Response time: 50 days.
Vigor: Medium.
Shelf life: Near 18 days.
Disease (susceptibility/resistance observed): None observed to date.
Pest (susceptibility/resistance observed): None observed to date.
Drought and temperature (susceptibility/resistance): None observed to date.
Growth retardant type and treatment: 1 application B9 after 7 days from commencement of Short Days at 1 gram/liter.
The plants were grown for 2 weeks in Long Day conditions (20 hours of light) and then transferred to Short Day conditions (13 hours of darkness).
Propagation:
- *Type.*—Vegetative Propagation via Stem Cuttings.
- *Time to rooting.*—12 days with soil temperatures of 22° C.
- *Rooting habit.*—Fine and Fibrous.

Foliage

Number of leaves per stem: 30–35.
Compound or single: Single.
Arrangement of leaves: Alternate.
- *Shape of leaf.*—Typically 5 lobed.
- *Size of leaf.*—Width: 4 cm–8.5 cm Length: 8 cm–14 cm.
- *Leaf apex.*—Mucronate.
- *Base.*—Truncate.
- *Attachment.*—Petioled.
- *Aspect.*—Slightly undulating.
- *Margin.*—Palmately lobed.
- *Surface characteristics.*—Top: Slightly Pubescent. Bottom: Slightly Pubescent.

Petiole:
- *Color.*—Near 137A.
- *Length.*—1 cm–3 cm.

Venation: Net. Mid vein prominent at underside.
- *Color.*—Upper side: near 138B under side: near 138B.

Color: Mature Leaf, upper side: near 138A; under side: near 138B. Young Leaf: upper side: near 139A; under side: near 139B.

Flower

Flower appearance: Matte.
Flower type: Decorative.
Flower form: Flat.
Flower shape: Round.
Flowering habit: Cyme.
Number of blossoms per branch: 1.
Inflorescence form: Corymbiform.
- *Depth of fully expanded blossoms.*—1.5 cm–2.5 cm.
- *Diameter of fully expanded blossoms.*—6.5 cm–9 cm.

Phyllaries:
- *Number.*—21–25.
- *Color.*—Near 137A.
- *Length.*—0.7 cm.–1.0 cm.
- *Width.*—0.2 cm–0.3 cm.
- *Texture/appearance.*—Dull/Slightly Pubescent.

Pedicel:
- *Length.*—7 cm–18 cm.
- *Diameter.*—0.2 cm–0.3 cm.
- *Angle from stem.*—20°–25°.
- *Color.*—Near 138B.
- *Surface.*—Pubescent.
- *Habit.*—Slightly curved.
- *Strength.*—Strong.

Ray florets:
*Form/shape.*—Straight.
*Texture/appearance.*—Slightly shiny and grooved.
*Number per flower.*—225–250.
*Length.*—1.5 cm–4.5 cm; Width: 0.7 cm–1.6 cm.
*Apex.*—Pointed.
*Base.*—Tubular.
*Margin.*—Entire.
*Disc florets.*—None observed.
Fragrance: Slight.
Flower bud (at onset of color):
*Length.*—0.7 cm–1.0 cm.
*Diameter.*—1.0 cm–1.5 cm.
*Form/shape.*—Ball shaped.
General flower color:
1. *Ray florets, upper side.*—Immature: near 155A. Mature: near 155C. Older/Fading: near 155C.
2. *Ray florets, under side.*—Immature: near 155A. Mature: near 155C. Older/Fading: near 155C.
3. *Bud.*—Near 139C.

Flower progression with age; color does not fade with age. The lastingness of bloom is about 18 days.

Reproductive Organs

Gynoecium present on ray florets only.
Ray florets per individual flower:
*Pistil number.*—125–175 observed.
*Stigma color.*—Near 14A.
*Stigma shape.*—Triple.
*Style color.*—Near 143C.
*Style length.*—0.2 cm–0.2 cm.
Androecium not observed.
Fruit and seeds: None observed.

What is claimed is:

1. A new and distinct variety of *Chrysanthemum* plant, substantially as described and illustrated herein.

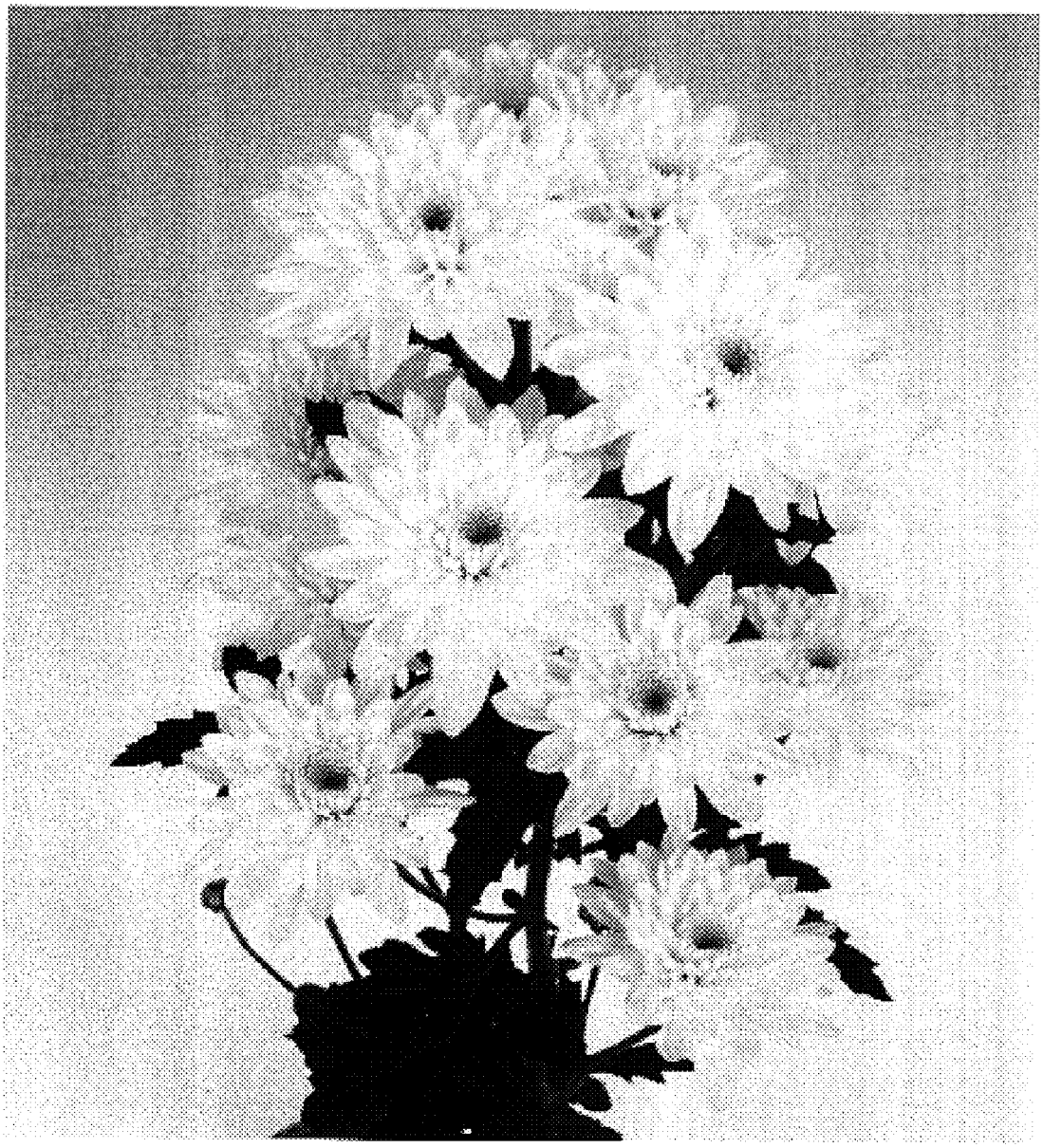

* * * * *